(12) United States Patent
Matuschka-Greiffenclau et al.

(10) Patent No.: US 8,633,192 B2
(45) Date of Patent: Jan. 21, 2014

(54) COMPOSITIONS AND USES THEREOF

(75) Inventors: Markus Matuschka-Greiffenclau, Bischofszell (CH); Haruhiko Inufusa, Osaka (JP)

(73) Assignee: TIMA Foundation, Balzars (LI)

( * ) Notice: Subject to any disclaimer, the term of this patent is extended or adjusted under 35 U.S.C. 154(b) by 748 days.

(21) Appl. No.: 11/956,407

(22) Filed: Dec. 14, 2007

(65) Prior Publication Data

US 2008/0161318 A1 Jul. 3, 2008

Related U.S. Application Data

(60) Provisional application No. 60/870,200, filed on Dec. 15, 2006.

(51) Int. Cl.
*A61K 31/525* (2006.01)
*A61K 31/44* (2006.01)
*A61K 31/19* (2006.01)

(52) U.S. Cl.
USPC ........... 514/251; 514/574; 514/561; 514/356; 514/474; 514/563

(58) Field of Classification Search
None
See application file for complete search history.

(56) References Cited

U.S. PATENT DOCUMENTS

| 4,006,219 A | * | 2/1977 | Upham et al. | 424/94.1 |
| 2002/0155163 A1 | | 10/2002 | Benjamin et al. | |
| 2005/0238638 A1 | * | 10/2005 | Gutwein | 424/125 |
| 2005/0271754 A1 | * | 12/2005 | Cochrane | 424/750 |

FOREIGN PATENT DOCUMENTS

| WO | WO-03006073 A1 | | 1/2003 |
| WO | WO-2005077464 A1 | | 8/2005 |
| WO | WO-2005/117924 | | 12/2005 |
| WO | WO2007/016949 | * | 2/2007 |

OTHER PUBLICATIONS

Hirsch, J Clin Endocrinol Metab. 87:975-977, 2002.*
Yahoo health: http://health.yahoo.com/addiction-resources/ascorbic-acid-vitamin-c/healthwise--d00426a1.html, revision date Feb. 13, 2004.*

* cited by examiner

*Primary Examiner* — Bong-Sook Baek
(74) *Attorney, Agent, or Firm* — Wilmer Cutler Pickering Hale and Dorr LLP

(57) ABSTRACT

Compositions and their use in the treatment or prevention of hyperglycemia and related diseases or disorders are disclosed.

7 Claims, 13 Drawing Sheets

|               | 1      | 2      | 3      | 4      | 5      | 6      | 7      | 8      | 9      | 10     |
|---------------|--------|--------|--------|--------|--------|--------|--------|--------|--------|--------|
| Vitamin C     | 1.0 g  | 1.0 g  | 2.0 g  | 2.0 g  | 1.0 g  | 1.0 g  | 1.5 g  | 1.5 g  | 1.0 g  | 1.0 g  |
| Cysteine      | 500 mg | 500 mg | 500 mg | 500 mg | 500 mg | 500 mg | 750 mg | 750 mg | 500 mg | 500 mg |
| Fumaric acid  | 100 mg | 100 mg | 100 mg | 100 mg | 200 mg | 200 mg | 100 mg | 100 mg | 150 mg | 150 mg |
| Succinic acid | 100 mg | 100 mg | 100 mg | 100 mg | 200 mg | 200 mg | 100 mg | 100 mg | 150 mg | 150 mg |
| Riboflavin    | 40 mg  | 40 mg  | 40 mg  | 40 mg  | 50 mg  | 50 mg  | 50 mg  | 50 mg  | 40 mg  | 40 mg  |
| Glutamine     | 1.5 g  |        |        |        |        |        | 1.5 g  | 1.5 g  |        |        |
| Glutamic acid |        | 1.5 g  | 1.0 g  | 1.0 g  | 1.0 g  | 1.0 g  |        |        | 1.0 g  | 1.0 g  |
| Niacin        | 10 mg  | 10 mg  | 10 mg  | 10 mg  | 10 mg  | 10 mg  | 15 mg  | 15 mg  | 10 mg  | 10 mg  |
| Coenzyme Q10  | 100 mg | 100 mg | 100 mg | 100 mg | 100 mg | 100 mg | 100 mg | 100 mg | 100 mg | 100 mg |

|               | 11     | 12     | 13     | 14     | 15     | 16     | 17     | 18     | 19     | 20     |
|---------------|--------|--------|--------|--------|--------|--------|--------|--------|--------|--------|
| Vitamin C     | 2.0 g  | 2.0 g  | 1.0 g  | 1.0 g  | 1.0 g  | 1.0 g  | 1.0 g  | 1.0 g  | 1.5 g  | 1.5 g  |
| Cysteine      | 1.0 g  | 1.0 g  | 500 mg | 500 mg | 500 mg | 500 mg | 750 mg | 750 mg | 500 mg | 500 mg |
| Fumaric acid  | 200 mg | 200 mg | 150 mg | 150 mg | 100 mg | 100 mg | 100 mg | 100 mg | 100 mg | 100 mg |
| Succinic acid | 200 mg | 200 mg | 150 mg | 150 mg | 100 mg | 100 mg | 100 mg | 100 mg | 100 mg | 100 mg |
| Riboflavin    | 60 mg  | 60 mg  | 20 mg  | 20 mg  | 40 mg  | 40 mg  | 50 mg  | 50 mg  | 50 mg  | 50 mg  |
| Glutamine     | 2.0 g  |        |        |        |        |        |        |        |        |        |
| Glutamic acid |        | 2.0 g  | 1.5 g  | 1.5 g  | 1.5 g  | 1.5 g  | 1.5 g  | 1.5 g  | 1.5 g  | 1.5 g  |
| Niacin        | 10 mg  | 10 mg  | 15 mg  | 15 mg  | 10 mg  | 10 mg  | 10 mg  | 10 mg  | 10 mg  | 10 mg  |
| Coenzyme Q10  | 100 mg | 100 mg | 100 mg | 100 mg | 120 mg | 120 mg | 120 mg | 120 mg | 120 mg | 120 mg |

Fig. 12a

| | 21 | 22 | 23 | 24 | 25 | 26 | 27 | 28 | 29 | 30 |
|---|---|---|---|---|---|---|---|---|---|---|
| Vitamin C | 1.0 g | 1.0 g | 1.0 g | 1.0 g | 1.0 g | 1.0 g | 500 mg | 500 mg | 500 mg | 500 mg |
| Cysteine | 500 mg | 500 mg | 500 mg | 500 mg | 500 mg | 500 mg | 200 mg | 200 mg | 200 mg | 200 mg |
| Fumaric acid | 100 mg | 100 mg | 100 mg | 100 mg | 100 mg | 100 mg | 100 mg | 100 mg | 50 mg | 50 mg |
| Succinic acid | 100 mg | 100 mg | 100 mg | 100 mg | 100 mg | 100 mg | 100 mg | 100 mg | 50 mg | 50 mg |
| Riboflavin | 30 mg | 30 mg | 50 mg | 50 mg | 40 mg | 40 mg | 30 mg | 30 mg | 50 mg | 50 mg |
| Glutamine | 1.5 g | | 1.0 g | 1.0 g | | | | 1.0 g | 1.0 g | |
| Glutamic acid | | 1.5 g | | | 1.5 g | 1.5 g | 1.0 g | | | 1.0 g |
| Niacin | 12 mg | 12 mg | 10 mg | 10 mg | 10 mg | 10 mg | 10 mg | 10 mg | 12 mg | 12 mg |
| Coenzyme Q10 | 80 mg | 80 mg | 80 mg | 80 mg | 80 mg | 80 mg | 80 mg | 80 mg | 100 mg | 100 mg |

| | 31 | 32 | 33 | 34 | 35 | 36 | 37 | 38 | 39 | 40 |
|---|---|---|---|---|---|---|---|---|---|---|
| Vitamin C | 1.0 g | 1.0 g | 1.0 g | 1.0 g | 1.0 g | 1.0 g | 500 mg | 500 mg | 500 mg | 500 mg |
| Cysteine | 500 mg | 500 mg | 500 mg | 500 mg | 500 mg | 500 mg | 500 mg | 500 mg | 500 mg | 500 mg |
| Fumaric acid | 500 mg | 500 mg | 250 mg | 250 mg | 100 mg | 100 mg | 100 mg | 100 mg | 250 mg | 250 mg |
| Succinic acid | 500 mg | 500 mg | 250 mg | 250 mg | 100 mg | 100 mg | 100 mg | 100 mg | 250 mg | 250 mg |
| Riboflavin | 40 mg | 40 mg | 50 mg | 50 mg | 40 mg | 40 mg | 40 mg | 40 mg | 50 mg | 50 mg |
| Glutamine | 1.5 g | | 1.0 g | 1.0 g | | | | 1.0 g | 1.0 g | |
| Glutamic acid | | 1.5 g | | | 1.5 g | 1.5 g | 1.0 g | | | 1.0 g |
| Niacin | 10 mg | 10 mg | 10 mg | 10 mg | 10 mg | 10 mg | 10 mg | 10 mg | 12 mg | 12 mg |
| Coenzyme Q10 | 100 mg | 100 mg | 100 mg | 100 mg | 100 mg | 100 mg | 100 mg | 100 mg | 100 mg | 100 mg |

Fig. 12b

COMPOSITIONS AND USES THEREOF

CROSS REFERENCE TO RELATED APPLICATIONS

This application claims the benefit of priority to U.S. Provisional Application No. 60/870,200, filed Dec. 15, 2006, the contents of which are incorporated by reference herein in their entirety.

BACKGROUND

Hyperglycemia is a condition associated with various diseases conditions. One of the most prominent disease states with hyperglycemia as a symptom is diabetes mellitus. Diabetes mellitus is a systemic disease which starts with continuous high levels of blood glucose. A healthy person typically controls the levels of blood glucose by the hormone insulin and keeps the blood glucose levels in between about 80 to about 100 mg/dl in hungry status. In patients with diabetes blood glucose levels can exceed 125 mg/dl.

Since the first therapeutic use of insulin, diabetes mellitus has been a treatable but chronic disease condition, and the main health risks are the characteristic long-term complications associated with the disease. These include an increased risk for cardiovascular diseases, chronic renal failure, retinal damage possibly resulting in blindness, nerve damage, erectile dysfunction (impotence) and gangrene with risk of amputation. One assay usually used to test for diabetes, but also for insulin resistance, is the glucose tolerance test. The glucose tolerance test in medical practice measures how quickly administered glucose is cleared from the blood. The glucose is most often given orally so the common test is technically an oral glucose tolerance test (OGTT). There are several drugs available for the treatment of diabetes. Oral drugs for the treatment of diabetes mellitus are classified in four categories. Within the first category are inhibitors of glucose absorption, e.g., alpha glucosidase inhibitors. In the second category are inhibitors of glucose production in the liver, e.g., biguanide. The third category includes drugs that improve the insulin sensitivity of the body, e.g., thiazolidine derivatives. To the fourth category belong stimulators of insulin secretion, e.g., sulfonyl urea or tenaglinid. These drugs are essentially dependent on the effects of insulin controlling glucose metabolism.

For improvement of the health status of an individual in general, numerous food supplements are available. Usually they are based on the use of vitamins and other metabolically relevant substances. Some of these also claim to be beneficial for patients suffering from diabetes or diabetes related conditions. For example, in US Patent application US 2002155163, it has been proposed that a daily multi-vitamin and mineral combination can be of use in the adjunct care of humans with diabetes. The composition comprises thiamin, riboflavin, niacin, vitamin B6, folate, vitamin B12, biotin, pantothenic acid, choline, inositol, para-amino benzoic acid, vitamin C, calcium, magnesium, iodine, selenium, manganese, chromium, molybdenum, boron, zinc, potassium, silicon, sulfur, vanadium, citrus bioflavonoid complex, hesperidin complex, rutin, vitamin A, vitamin D, vitamin E, lycopene, lutein, coenzyme Q10 and alpha-lipoic acid. In another example it has been proposed to use for treatment of diabetic neuropathy a pharmaceutical composition comprising as active ingredients vitamin C, vitamin E, Gingko biloba and at least one substance selected from the group consisting of a vitamin, a mineral, an amino acid and a herb, and also includes a physiologically acceptable pharmaceutical carrier or diluent (WO 2005/117924).

In the past, the common practice to include numerous metabolically relevant ingredients in food supplements for improvement of nutrition and to promote general well being has led to compositions comprising dozens of substances without verification of whether these substances in combination really provide beneficial effects for the patient or not. Even worse, sometimes the erratic combination of unlimited ingredients can cause serious adverse effects in the consumer. Therefore, it becomes more and more apparent that the ingredients in such compositions should preferably not be combined at random but selected carefully and based on profound knowledge.

Thus, for the prevention and/or treatment of hyperglycemia-related diseases such as diabetes there is still a need for drugs and compositions that are easy to administer and that are pharmaceutically acceptable and have no or little adverse effects. In particular, drugs are needed that do not rely (or rely only to a small extent) on the effects of insulin, and that comprise a reasonable number of ingredients. Therefore, it is an object of the present invention to provide compositions effective in reducing blood glucose for the treatment and/or prophylaxis of hyperglycemia-related diseases such as diabetes.

BRIEF SUMMARY OF THE INVENTION

It has been discovered that administration of a composition that includes vitamin C, glutamic acid and/or glutamine, cysteine, riboflavin, succinic acid, fumaric acid, coenzyme Q10 and niacin reduces blood glucose levels. This discovery has been exploited to develop the present invention, which is directed, at least in part, to compositions and to methods of treating, preventing, or delaying the onset of symptoms of hyperglycemia and/or hyperglycemia-related diseases, e.g., diabetes.

Accordingly, in one aspect, the invention features a composition that includes one or more of glutamic acid, glutamine, a prodrug thereof, or a salt thereof, one or more of cysteine, a prodrug thereof, or a salt thereof, one or more of riboflavin, a prodrug thereof, or a salt thereof, one or more of succinic acid, a prodrug thereof, or a salt thereof, one or more of fumaric acid, a prodrug thereof, or a salt thereof, one or more of niacin, a prodrug thereof, or salt thereof, one or more of coenzyme Q10, a prodrug thereof, or a salt thereof, and optionally one or more of vitamin C, a prodrug thereof, or a salt thereof. In one embodiment, the composition includes other components.

In another embodiment, the composition does not include additional components. For example, the composition does not include any additional vitamins, amino acids, organic acids, nucleotides, polysaccharides, oligosaccharides, disaccharides or monosaccharides.

In some embodiments, the composition includes about 0.01 g to about 50 g, e.g., about 0.1 g to about 10 g, e.g., about 0.25 g to about 5 g, e.g., about 0.5 g to about 3 g, e.g., about 0.75 g to about 2 g, e.g., about 1.5 g of glutamic acid, of glutamine, or of a combination of glutamic acid and glutamine.

In some embodiments, the composition includes about 0.01 g to about 50 g, e.g., about 0.1 g to about 10 g, e.g., about 0.2 g to about 5 g, e.g., about 0.25 g to about 3 g, e.g., about 0.3 g to about 1 g, e.g., about 0.5 g of cysteine.

In other embodiments, the composition includes about 0.001 g to about 50 g, e.g., about 0.005 g to about 10 g, e.g., about 0.01 g to about 1 g, e.g., about 0.01 g to about 0.1 g, e.g., about 0.04 g of riboflavin.

In some embodiments, the composition includes about 0.001 g to about 50 g, e.g., about 0.001 g to about 10 g, e.g., about 0.01 g to about 2 g, e.g., about 0.01 g to about 1 g, e.g., about 0.1 g of succinic acid.

In yet other embodiments, the composition includes about 0.001 g to about 50 g, e.g., about 0.001 g to about 10 g, e.g., about 0.01 g to about 2 g, e.g., about 0.01 g to about 1 g, e.g., about 0.1 g of fumaric acid.

In other embodiments, the composition includes about 0.001 g to about 50 g, e.g., about 0.001 g to about 10 g, e.g., about 0.001 g to about 1 g, e.g., about 0.001 g to about 0.1 g, e.g., about 0.001 g to about 0.05 g, e.g., about 0.001 g to about 0.03 g, e.g., about 0.005 g to about 0.02 g, e.g., about 0.01 g to about 0.015 g of niacin. In some embodiments, the composition includes about 0.005 g, about 0.01 g, about 0.015 g, or about 0.02 g niacin.

In some embodiments, the composition includes about 0.001 g to about 50 g, e.g., about 0.001 g to about 10 g, e.g., about 0.01 g to about 2 g, e.g., about 0.01 g to about 1 g, e.g., about 0.25 g of coenzyme Q10.

In yet other embodiments, the composition optionally includes about 0.01 g to about 50 g, e.g., about 0.1 g to about 10 g, e.g., about 0.25 g to about 5 g, e.g., about 0.5 g to about 3 g, e.g., about 0.75 g to about 1.5 g, e.g., about 1 g vitamin C.

In one embodiment, the composition includes about 1.5 g of glutamic acid, about 1.5 g of glutamine, or about 1.5 g of a combination of glutamic acid and glutamine; about 0.5 g of cysteine; about 0.04 g of riboflavin; about 0.1 g of succinic acid; about 0.1 g of fumaric acid; about 0.01 g of niacin; about 0.25 g of coenzyme Q10; and about 1 g of vitamin C.

In other embodiments, the composition is one of the compositions described in FIG. 12.

In a preferred embodiment, the composition does not include glucose. In other embodiments, the composition does not include vitamin C.

In some embodiments, the composition is in tablet form, capsule form, powder form, or liquid form.

In another aspect, the invention features a food supplement that includes a composition described herein. The supplement can be consumed, e.g., before, simultaneously with, or after consumption of food or drinks. In some embodiments, the food or drinks contain carbohydrates, e.g., a high level of carbohydrates.

In some embodiments, the supplement can include further substances, such as vitamins, amino acids or other metabolically important substances. However, in a particular preferred embodiment, the supplement includes a composition described herein but does not include any additional vitamins, amino acids, organic acids, nucleotides, polysaccharides, oligosaccharides, disaccharides or monosaccharides. In a preferred embodiment, the supplement contains no glucose.

In some embodiments, the supplement is for human use. In other embodiments, the supplement is for non-human use, e.g., as a supplement in animal food, e.g., pet food.

In another aspect, the invention features a pharmaceutical composition that includes a composition described herein. In some embodiments, the pharmaceutical composition includes a pharmaceutically acceptable carrier, excipient or diluent, e.g., a pharmaceutically acceptable carrier, excipient or diluent described herein.

In another aspect, the invention features a method of treating or preventing hyperglycemia in a subject. The method includes administering to the subject a composition, food supplement or pharmaceutical composition described herein, e.g., a therapeutically effective amount of a composition, food supplement or pharmaceutical composition described herein, to treat or prevent hyperglycemia in the subject.

In some embodiments, the hyperglycemia is incident to consuming food and/or drinks. In other embodiments, the hyperglycemia is an abnormal level of hyperglycemia as a result of, e.g., a disease or disorder. In some embodiments, the subject has or is suffering from hyperglycemia. In other embodiments, the subject is at risk of developing hyperglycemia. In some embodiments, the composition, supplement or pharmaceutical composition is administered in combination with one or more additional therapies for hyperglycemia.

In another aspect, the invention features a method of treating or preventing a hyperglycemia-related disease or disorder in a subject in need thereof. The method includes administering to the subject a composition, food supplement or pharmaceutical composition described herein, e.g., a therapeutically effective amount of a composition, food supplement or pharmaceutical composition described herein, to treat or prevent the hyperglycemia-related disease or disorder.

The hyperglycemia-related disease or disorder can be, e.g., Type I diabetes mellitus, Type II diabetes mellitus, steroid diabetes, gestational diabetes, secondary diabetes, Morbus Basedow, acromegaly, acute heart attack, hyperfunction of the adrenal gland, phaeochromocytoma, inhalation anaesthesia, shock, carbon monoxide poisoning, meningitis, a craniocerebral injury, a brain tumor, idiopathic hyperglycemia, impaired fasting glycemia (IFG) or impaired glucose tolerance (IGT). In some embodiments, the subject has or is suffering from a hyperglycemia-related disease or disorder described herein. In other embodiments, the subject is at risk of developing a hyperglycemia-related disease or disorder described herein. In some embodiments, the composition, supplement or pharmaceutical composition is administered in combination with one or more additional therapies for a hyperglycemia-related disease or disorder.

In another aspect, the invention features a method of treating diabetes in a subject. The method includes administering to the subject a composition, food supplement or pharmaceutical composition described herein, e.g., a therapeutically effective amount of a composition, food supplement or pharmaceutical composition described herein, to treat diabetes. In some embodiments, the composition, food supplement or pharmaceutical composition is administered in combination with one or more additional therapies for diabetes, e.g., insulin therapy, thereby treating diabetes in the subject.

In another aspect, the invention features a method of preventing or delaying onset of symptoms of diabetes in a subject. The method includes administering to a subject at risk of developing diabetes a composition, food supplement or pharmaceutical composition described herein, e.g., a therapeutically effective amount of a composition, food supplement or pharmaceutical composition described herein, to treat diabetes.

In another aspect, the invention features a method of preventing or delaying onset of symptoms of diabetes in a subject. The method includes identifying a subject at risk of developing diabetes, and administering to the subject a composition, food supplement or pharmaceutical composition described herein, e.g., a therapeutically effective amount of a composition, food supplement or pharmaceutical composition described herein, thereby preventing or delaying onset of symptoms of diabetes in the subject.

In some embodiments, the identifying step includes evaluating the subject for the presence of a risk factor for developing diabetes, e.g., a risk factor described herein.

Definitions

The term "hyperglycemia", as used herein, refers to any elevated level of blood glucose compared to a basal level in a subject. "Basal level", as used herein, refers to a blood glucose level of a normal subject when fasting. Generally, hyperglycemia refers to blood glucose levels above about 100 mg/dl. In particular, hyperglycemia refers to blood glucose levels above about 110 mg/dl when fasting and above about 140 mg/dl two hours after having a meal.

The term "hyperglycemia-related disease or disorder", as used herein, refers to a disease or disorder that has, as a symptom, inappropriately elevated blood glucose levels (i.e., exhibits hyperglycemia), and to a disease or disorder that can be the consequence of hyperglycemia, e.g., repeated or chronic hyperglycemia. Non-limiting exemplary hyperglycemia-related diseases and disorders include several forms of diabetes (in particular Diabetes mellitus of type I and II, steroid diabetes (Morbus Cushing), gestational diabetes, and secondary diabetes induced by other disease states (e.g., pancreatitis, obesity)), Morbus Basedow, acromegaly, acute heart attack, hyperfunction of the adrenal gland, phaeochromocytoma, inhalation anaesthesia, shock, carbon monoxide poisoning, disorders of the central nervous system (such as meningitis, craniocerebral injury, brain tumors etc.) and idiopathic hyperglycemia in new born children.

The term "diabetes", as used herein, refers to any kind of diabetes associated with high blood glucose levels. "Diabetes" includes, e.g., diabetes mellitus of type I and II, steroid diabetes (Morbus Cushing), gestational diabetes and kinds of secondary diabetes induced by other disease states (e.g., pancreatitis, obesity).

"Dosage form", as used herein, refers to an amount of medication to be taken at one time, optionally in regular intervals.

The term "supplement", as used herein, refers to a composition that is consumed in addition to meals or drinks. Consumption of the supplement can occur before, simultaneously or after uptake of the meal or drinks. If consumption occurs simultaneously to the meal or drink, then the supplement can be an ingredient, i.e., additive, of the respective meal or drink itself, or can be consumed from a source different than the meal or drink. "Ingredient", as used herein, is a substance or component that forms part of a composition.

The term "prodrug", as used herein, refers to a substance that is converted into at least one active ingredient of a composition described herein as a consequence of metabolization of the substance after uptake by a human or animal. The term is not intended to refer to substances that yield after metabolization only to a negligible extent one of the active ingredients of the compositions described herein. For example, proteins and peptides are digested during metabolization into individual amino acids. Thus, while a protein or peptide rich in glutamic acid, glutamine and/or cysteine can function as a prodrug, only proteins or peptides with about average or slightly elevated frequency of glutamic acid, glutamine and/or cysteine are considered to be a prodrug for said substances. In particular, the term "prodrug" refers to a substance that is metabolized into an active ingredient of a composition described herein within 5, preferably 4, even more preferably 3, even more preferably 2, and most preferably within 1 metabolic reaction(s).

The term "treatment" or "treating", as used herein, refers to administering a therapy in an amount, manner, and/or mode effective to improve a condition, symptom, or parameter associated with a disease or disorder or to prevent or reduce progression of a disease or disorder, either to a statistically significant degree or to a degree detectable to one skilled in the art. An effective amount, manner, or mode can vary depending on the subject and may be tailored to the subject.

The expression "a subject in need thereof", as used herein, refers to a human or non-human animal that is in need of treatment for one or more diseases or disorders described herein. A "subject in need thereof" may be a human or non-human animal having one or more symptoms of a disease or disorder described herein, or having or exhibiting a risk factor for a disease or disorder described herein. Such a subject may be, but is not necessarily, a human or non-human animal that has received a clinical diagnosis of one or more diseases or disorders described herein.

BRIEF DESCRIPTION OF THE DRAWINGS

The foregoing and other objects of the present invention, the various features thereof, as well as the invention itself, may be more fully understood from the following description, when read together with the accompanying drawings, in which:

FIG. 12A and FIG. 12B are lists of examples of compositions described herein.

DETAILED DESCRIPTION

Figure 1:
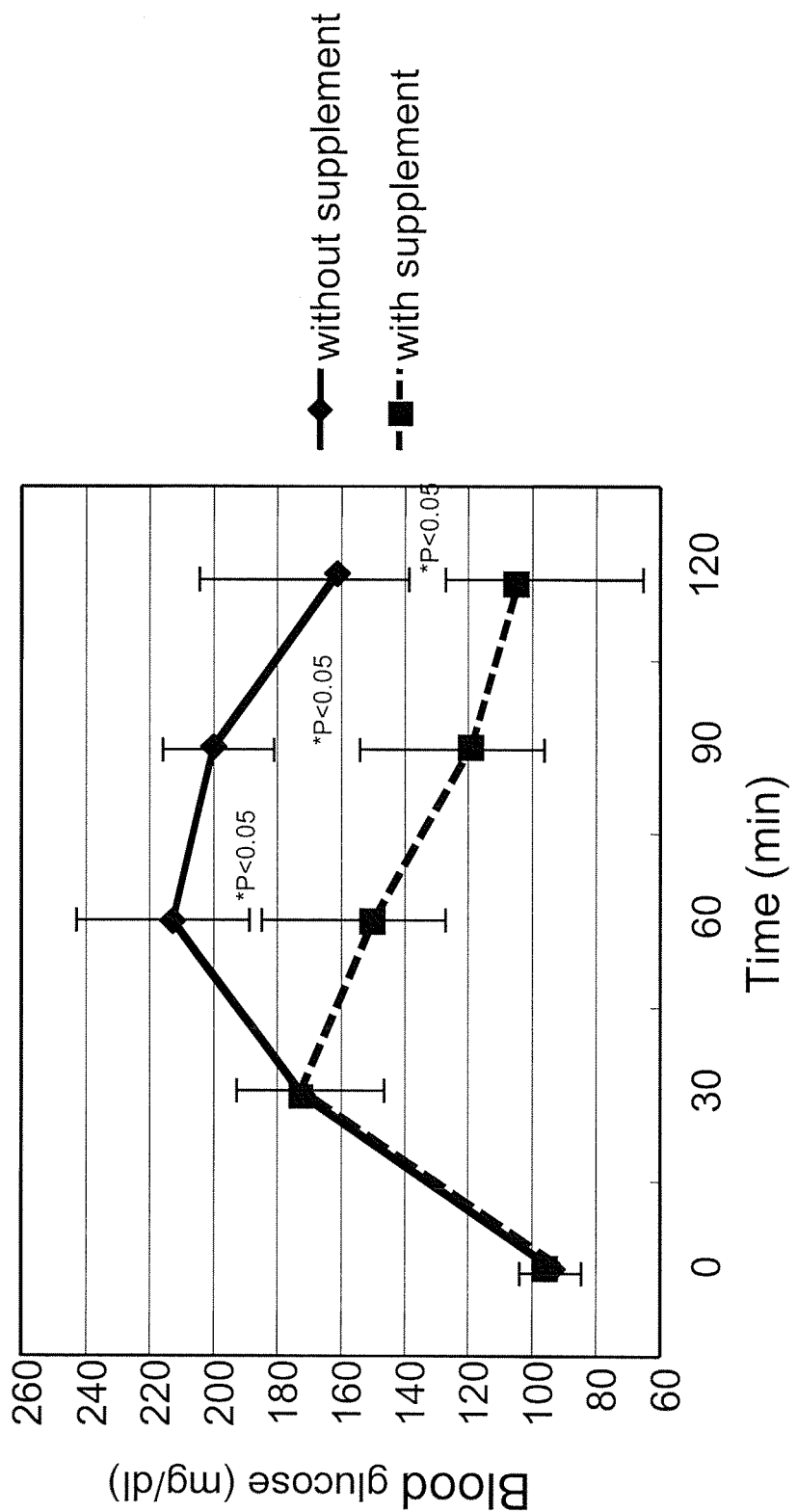
FIG. 1 is a graph of blood glucose levels during an oral glucose tolerance test (OGTT) with or without supplement.

The present invention features compositions that can be, e.g., supplements (e.g., dietary or food supplements) or pharmaceuticals, methods of treating subjects having hyperglycemia or hyperglycemia-related diseases with the compositions described herein, and methods of treating and/or preventing hyperglycemia and/or hyperglycemia-related diseases in subjects by administering such compositions. As described herein, the compositions can include one or more of glutamic acid, glutamine, a prodrug thereof, or a salt thereof, one or more of cysteine, a prodrug thereof, or a salt thereof, one or more of riboflavin, a prodrug thereof, or a salt thereof, one or more of succinic acid, a prodrug thereof, or a salt thereof, one or more of fumaric acid, a prodrug thereof, or a salt thereof, one or more of niacin, a prodrug thereof, or salt thereof, one or more of coenzyme Q10, a prodrug thereof, or a salt thereof, and optionally one or more of vitamin C, a prodrug thereof, or a salt thereof.

Vitamin C, also called ascorbic acid is used by the body for many purposes. By far its main purpose is to function as a reducing agent. In the compositions described herein, vitamin C (ascorbic acid) as well as its salts, e.g., ascorbate salts, can be used.

Glutamic acid is a non-essential amino acid. It plays an important role in human metabolism and can function as a neurotransmitter. Because of the latter it is often used in food supplements. In the compositions described herein, glutamic acid as well as its salts, e.g., glutamate salts, can be used.

Glutamine is a non-essential amino acid which plays, besides an important component of proteins, an important role in nitrogen metabolism. It is used as a supplement in weightlifting, bodybuilding, endurance and other sports, as well as by those who suffer from muscular cramps or pain— particularly by elderly people. In the compositions described herein, glutamine as well as a salt of glutamine can be used.

Cysteine is a naturally occurring amino acid that has a thiol group and is found in most proteins. When exposed to air, cysteine oxidizes to form cystine, a dimer of two cysteine molecules joined by a weak disulfide bond. As a sulfur-based amino acid, cysteine itself can act as an antioxidant in the body. Cysteine is an important source of sulfur in human metabolism, and although it is classified as a non-essential amino acid, cysteine may be essential for infants, the elderly, and individuals with metabolic disease or who suffer from malabsorption syndromes. Cysteine may at some point be recognized as an essential or conditionally essential amino acid. In the compositions described herein cysteine, salts thereof, and cystine can be used. In some instances, cystine is used as an exemplary prodrug for cysteine.

Riboflavin (vitamin B2) is an essential compound for higher animals including humans. Riboflavin is commercially used as a vitamin preparation for use in vitamin deficiency and as a food supplement. In addition, it is also employed as a food dye, for example, in mayonnaise, ice cream etc. Riboflavin can be prepared either chemically or microbiologically and can be obtained from several manufacturers. Biologically active riboflavin is flavin mononucleotide (FMN) or flavin adenine dinucleotide (FAD). These active forms and their reduced forms, FMNH2 and FADH2, can all be used in the compositions described herein.

Succinic acid, also termed butanedioic acid, amber acid and E 363, is used as food supplement, for example, as a substitute for cooking salt in dietary meals or as a flavour enhancer. In the citric cycle, the salt of succinic acid, succinate, is involved in regeneration of the acceptor oxalate. In the compositions described herein, succinic acid, as well as succinate and its anhydrated form, succinic anhydride, can be used.

Fumaric acid, also termed 2-butenedioic acid, allomaleic acid, boletic acid and lichenic acid, is used as flavouring and thus is a common component of food additives and dietary supplements. In the compositions described herein, fumaric acid as well as its salts, e.g., fumarate salts, can be used.

Coenzyme Q10, also known as CoQ10, ubiquinone-10 and ubiquinone 50, is the most common CoQ in human mitochondria. There it is involved in the electron transport chain. It is used as supplement because of its antioxidant function.

Niacin is also known as nicotinic acid (nicotinate) and vitamin B3. The term also includes the amide form, nicotinamide or niacinamide. Its biologically active forms, nicotinamide adenine dinucleotide (NAD) and nicotinamide adenine dinucleotide phosphate (NADP), as well as their reduced forms, NADH and NADPH, play essential roles in the metabolism of any living being. Nicotinamide mononucleotide (NMN), desamido-NAD and deamino-NAD (also known as nicotinamide hypoxanthine dinucleotide) are metabolic intermediates containing the niacin molecule. All of these forms can be used in the compositions described herein. NAD, NADH, NADP, NADPH, NMN, deamido-NAD, and/or deamino-NAD containing niacin molecules can also be used in the compositions described herein.

Proteins and peptides, i.e., polymers of amino acids, are easily digested in the small intestine. Therefore, proteins and peptides consisting to a significant extent of cysteine, glutamic acid and/or glutamine and combinations thereof can also be used in the compositions described herein. For example, proteins and peptides having an amino acid frequency of 30, 35, 40, 50 or more percent of cysteine, glutamine and/or glutamic acid can function as prodrugs and can be used, alternatively or in addition to glutamic acid, glutamine and/or cysteine, in the compositions described herein. The amino acid content of an unknown peptide and/or protein can be determined by, e.g., an amino acid analyzer. In the case of synthetically produced peptides, the amount of a specific type of amino acid is known from the design of the synthetic peptide. Using the molecular weight of the peptide, e.g., synthetic peptide, the molecular weight of the desired amino acid and the number of residues of the desired species of amino acid within the peptide, e.g., synthetic peptide, one of ordinary skill in the art can easily determine the amount of the peptide, e.g., synthetic peptide, needed for a dose of a composition described herein.

Supplements

The compositions described herein can be supplements and can be consumed before, simultaneously with, or after consumption of food or drinks, such as food or drinks with elevated carbohydrate content. The supplements can exist as various formulations.

For example, in one formulation, the supplements described herein can be a liquid in which a composition described herein is present in a dosage effective to reduce blood glucose levels to basal levels after consumption of food or drink. The liquid can be, e.g., a syrup-type liquid, which can be added to the food or drink. Alternatively, the liquid can be consumed on its own. In some instances, the supplement is a liquid that is diluted, e.g., in water, before consumption.

In another formulation, the supplement is a tablet or capsule. For example, such a tablet or capsule can be in a shape and of such dimension to facilitate swallowing. Alternatively, the tablets or capsules can be dissolved in a liquid, e.g., water, for consumption. Each tablet or capsule can contain a sufficient dosage of a supplement to reduce blood glucose levels after consumption of food or drinks. In other cases, an effective dosage includes a plurality of tablets and/or capsules. In such cases, the tablets and/or capsules can be packaged within a dosage receptacle that includes an appropriate number of tablets and/or capsules.

In other formulations, the components of supplements described herein can exist separately, e.g., in separate liquids, capsules or tablets. For example, it is possible to provide one formulation, for example a capsule, that includes a subset of components, and a second formulation, for example a second capsule, that includes the remaining components. In such instances, it is preferable that the separate formulations are consumed simultaneously or in close time intervals.

The tablets or capsules can also include suitable carrier substances, examples of which will are known to those of ordinary skill in the art. Exemplary carrier substances are sorbitol, gum acacia, calcium phosphate, alginates, microcrystalline cellulose, polyvinylpyrrolidone, cellulose, gelatine, and methyl cellulose.

In other situations, the supplement can be formulated into a cube form or a soft gel.

In other formulations, the supplement is a powder, e.g., a cryopowder. The powder can be added to food and/or a liquid directly, or the powder can be first dissolved, e.g., in water, prior to use.

The formulations may include additives such as sweeteners, flavorings, preservatives, stabilizers, colorings and pigments. In preferred formulations, such additives are not based on glucose compounds. Exemplary additives include fruit juice extracts, curcuma, tannin, a powder of Panax notoginseng, and Vinca rosea in suitable amounts. Other additives include Oolong tea, aloe vera and spiral water algae.

In some instances, the supplement is prepared in a manner that is compatible with a diabetic diet. For example, a diabetic diet can include limiting the consumption of sweets, increasing the number of meals per day (while reducing the amount consumed per meal), monitoring the amount and type of carbohydrates consumed, adding into the meal whole-grain foods, fruits and/or vegetables, consuming less fat, and reducing or ending consumption of alcohol. In particular, if the diabetic diet includes an increase in the number of meals per day, a supplement described herein can also be consumed in parallel to each meal, and preferably formulated accordingly.

In some instances, the supplement is formulated for consumption in regular intervals by a subject in need thereof. For example, the supplement can be formulated for daily consumption, for consumption ever other day, for weekly consumption, for consumption several times a day (e.g., 2, 3, 4, 5 or more times a day) or for any other dosing regimens appropriate for the health status of the subject.

In other instances, the supplement is consumed prior to consumption of a meal and/or a drink. In particular, the supplement can be consumed about 5 minutes, about 10 minutes, about 15 minutes, about 20 minutes, about 25 minutes, about 30 minutes, about 40 minutes, about 45 minutes, about 60 minutes, about 120 minutes or even earlier before having a meal and/or a drink. Particularly preferred is the consumption of the supplement about 20 to about 30 minutes before consumption of a meal and/or drink.

Pharmaceutical Compositions

The compositions described herein can be formulated as pharmaceutical compositions, e.g., with an appropriate solid or liquid pharmaceutically acceptable carrier, excipient or diluent. Such pharmaceutically acceptable carriers, excipients and diluents are conventional and known to those of ordinary skill in the art (see, e.g., Harrison's Principles of Internal Medicine, 14th Edition, McGraw-Hill, 1998). One example of a carrier is a vehicle of physiological saline solution, but it is contemplated that other pharmaceutically acceptable carriers such as physiological concentrations of other non-toxic salts, sterile water or the like may also be used. In some cases, it is desirable to use a suitable buffer.

Some examples of suitable carriers, excipients, and diluents include lactose, sorbitol, mannitol, gum acacia, calcium phosphate, alginates, calcium silicate, microcrystalline cellulose, polyvinylpyrrolidone, cellulose, gelatin, syrup, methyl cellulose, methyl-and propylhydroxybenzoates, talc, magnesium, stearate, water, mineral oil, and the like. The pharmaceutical compositions can additionally include lubricating agents, wetting agents, emulsifying and suspending agents, preserving agents, sweetening agents or flavoring agents. The pharmaceutical compositions may be formulated so as to provide rapid, sustained, or delayed release of the active ingredients after administration to the subject by employing procedures well known in the art. The formulations can also contain substances that diminish proteolytic degradation and promote absorption such as, for example, surface active agents.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Excipients can also be those substances usually and customarily employed to formulate dosages for continuous or periodic infusion.

The compositions described herein can also be formulated using drug carriers to improve, e.g., half-life in vivo, shelf life, bioavailability, or taste. In some situations, the compositions can be formulated to facilitate application of the composition and/or targeted delivery of the agent to a specific tissue or to a specific site of pharmacological action. For example, the composition can be incorporated into a nanoparticle, a nanoemulsion, a liposome, a prodrug, a polymeric micelle, or a colloidal drug carrier, e.g., as a component of a controlled release drug delivery system (see, e.g., Remington, The Science and Practice of Pharmacology, 20th Edition, Lippincott Williams & Wilkins, 2000).

The dosage form of the pharmaceutical composition will be determined by the mode of administration chosen. For instance, in addition to oral formulations, injectable fluids and topical formulations can be employed. Oral formulations can be liquid (e.g., syrups, solutions, or suspensions), or solid (e.g., powders, pills, tablets, or capsules). Topical preparations can include eye drops, ointments, sprays, and the like. For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

Administration

The compositions described herein can be administered to humans or other animals in various manners know to those with skill in the art, e.g., orally, intravenously, intraperitoneally, and intrathecally (see, e.g., Harrison's Principles of Internal Medicine, 14th Edition, McGraw-Hill, 1998). For oral administration, the pharmaceutical compositions can be formulated as described above for the supplement. The particular mode of administration and the dosage regimen can be selected by an attending physician, taking into account the particulars of the case (e.g., the subject and the disease state involved).

The pharmaceutical compositions can be administered when the blood glucose levels or insulin levels are already elevated, but can also be administered in advance if the blood glucose levels or insulin levels are expected to rise in the near future (e.g., as a consequence of having a meal) or if any rise of the blood glucose level or blood insulin level would be detrimental for the health and/or status of the patient. In the latter case (detrimental effect) the pharmaceutical composition can be administered to anticipate and prevent peaks of blood glucose levels and/or insulin levels.

In some instances, the pharmaceutical composition is formulated for administration in regular intervals to a subject in need thereof. For example, the pharmaceutical composition can be formulated for daily administration, for administration every other day, for weekly administration, for administration several times a day (such as two, three, four, five or more times a day) or for any other dosing regimen appropriate for the health status of the subject. In particular, the pharmaceutical composition can be formulated for administration prior to food uptake.

In other instances, the pharmaceutical composition is administered prior to consumption of a meal and/or a drink, in particular about 5 minutes, about 10 minutes, about 15 minutes, about 20 minutes, about 25 minutes, about 30 minutes, about 40 minutes, about 45 minutes about 60 minutes, about 120 minutes or even earlier before having a meal and/or a drink. Preferably, the pharmaceutical composition is administered about 20 to about 30 minutes before consumption of the meal and/or drink.

Combination Therapy

In some instances, the pharmaceutical compositions described herein can be administered in combination with a second pharmaceutical composition or with another method of treatment. In the case of treatment of diabetes, the second pharmaceutical composition or method of treatment can, for example, include administering inhibitors of glucose absorption (e.g., alpha glucosidase inhibitors), inhibitors of glucose production in the liver (e.g., biguanide), drugs improving the insulin sensitivity improving drugs (e.g., thiazolidine derivatives) and/or stimulators of insulin secretion (e.g., sulfonyl urea and/or tenaglinid). Preferably, the pharmaceutical composition is also compatible with a diabetic diet, such as described herein, or other dietary therapy approaches to reduce or prevent hyperglycemia. This combined administration is particularly preferred if the composition does not include vitamin C. In this embodiment, the medicament can be combined for example with a further pharmaceutical composition or method of treatment affecting blood glucose levels but not or only insufficiently blood insulin levels.

In particular the compositions described herein can be used when a person is already being treated with insulin in regular intervals. In this combination therapy, administration of a composition described herein can reduce the amount of insulin that may need to be administered to the patient compared to the level of insulin that must be administered in the absence of a composition described herein. This reduces, for example, the health costs of diabetic treatments. Therefore, the compositions described herein can be formulated to be administered in combination with insulin.

Diseases and Disorders

The compositions described herein can be administered to subjects to reduce elevated glucose levels and/or insulin levels in the blood of a subject in general, and in particular for the prevention and/or treatment of hyperglycemia and hyperglycemia-related disease conditions such as diabetes, e.g., diabetes mellitus of type I and/or II, steroid diabetes (Morbus Cushing), gestational diabetes and secondary diabetes induced by other disease states (e.g., pancreatitis, obesity); Morbus Basedow, acromegaly, acute heart attack, hyperfunction of the adrenal gland, phaeochromocytoma, inhalation anaesthesia, shock, carbon monoxide poisoning, disorders of the central nervous system (such as meningitis, craniocerebral injury, and brain tumours) and idiopathic hyperglycemia in new born children, as well as for reducing the risk for onset or progression of the aforementioned diseases by moderating glucose metabolism within the body.

The compositions described herein can also be used in the treatment of impaired fasting glycaemia (IFG) and/or impaired glucose tolerance (IGT) or other pre-diabetes disease states. IFG and IGT can both precede diabetes by years. The compositions described herein can thus be used to reduce elevated glucose levels in the blood of a subject affected by these pre-diabetic disease conditions in order to prevent onset of a true diabetic condition. Naturally, the compositions described herein can also be used as prophylactic agents if a subject exhibits genetic risk factors increasing the risk for development of a hyperglycemia-related disease or disorder such as a diabetic condition. Such risk factors are described herein, and include, for example, mutations of insulin, insulin receptor genes and other insulin metabolism pathway genes.

Subjects

The compositions described herein can be administered to any kind of subject, e.g., human or non-human animals, in need thereof, regardless of age or gender. In veterinary medicine, for example, cats, dogs, birds, cattle, horses, rodents and so forth can be treated.

In certain methods described herein, a composition described herein is administered to a subject at risk of developing diabetes. Such subjects can be identified by, e.g., evaluating the subject for the presence of risk factors, e.g., genetic risk factors, for diabetes.

Such risk factors are known in the art and can include, e.g., HLA-DR3, HLA-DR4, and HLA-DR3/HLA-DR4 phenotypes. Other risk factors are described in U.S. Pat. Nos. 6,902,888, 7,173,119, 6,326,141, 6,316,209, 6,291,172, 6,274,549, 5,908,627, 5,786,221, 5,407,802, and 5,200,318. In both humans and diabetes-prone non-obese diabetic (NOD) mice, genes mapping to the major histocompatibility complex have been associated with susceptibility to diabetes and shown to be very important in the disease process (Todd, Immunol. Today 11:122, 1990). Studies of NOD mice have mapped at least 12 other susceptibility genes to specific chromosomal locations (Prochazka et al., Science 237:286, 1987; Todd et al., Nature 351:542, 1991; De Gouyon et al., Proc. Nat. Acad. Sci. USA 90:1877, 1993; Morahan et al., Proc. Nat. Acad. Sci. USA 91:5998, 1994; Serreze et al., J. Exp. Med. 180:1553, 1994; Cornall et al., Nature 353:262, 1991; Garchon et al., Nature 353:260, 1991). In humans, markers near the insulin/insulin-like growth factor loci have also been associated with diabetes (Bell et al., Diabetes 33:176, 1984). Genome-wide searches and analyses of specific genes have identified at least 17 loci that contribute to the disease (Concannon et al., Nat Genet 19:292-6, 1998; Hashimoto et al., Nature 371:161-4, 1994; Davies et al., Nature 371:130-136, 1994; Mein et al., Nat Genet 19:297-300, 1998; Verge et al., J. Clin. Invest. 102:1569-1575, 1998). Significant evidence for linkage was reported for an about 7 cM region on chromosome 1q42-43 (Concannon et al., Nat Genet 19:292-6, 1998), containing the angiotensinogen (AGY) gene. Any of these genes, as well as others known in the art, can be used as markers for identifying a subject at risk for developing diabetes.

Those skilled in the art will recognize, or be able to ascertain, using no more than routine experimentation, numerous equivalents to the specific substances and procedures described herein. Such equivalents are intended to be encompassed in the scope of the claims that follow the examples below.

EXAMPLES

Example 1

Supplement and Volunteers

A supplement was prepared by mixing together one gram of vitamin C, 1.5 gram of glutamic acid, 500 mg of cysteine, 40 mg of riboflavin, 100 mg of succinic acid, 100 mg of fumaric acid, and 10 mg of niacin, and 250 mg of AQUAQ10P40 (100 mg of coenzyme Q10). All ingredients of the supplement, except coenzyme Q10, were purchased from Sigma Aldrich Japan (Tokyo, Japan). AQUAQ10P40 (Nissin Pharma, Tokyo Japan), which contains 40% by volume of coenzyme Q10, was used as coenzyme Q10. In the experiments for the comparison of the effects of glutamic acid and glutamine, glutamine was used in the supplement instead of glutamic acid in an analogous manner. The supplement was taken by the volunteers with 100 ml water 20 minutes before starting the oral glucose tolerance test.

Four volunteers, age 26-48 years old (average 38 years old), weight 45-75 kg (average 62 kg), two female and two male participated in the experiments. All volunteers were confirmed by blood test before the experiments to have neither diabetes mellitus nor liver dysfunction.

Standard oral glucose tolerance test (OGTT) was performed using 75 grams of D-glucose dissolved in water. The experiments were conducted with volunteers which were at least for more than 7 hours on fasting conditions and consequently hungry. The D-glucose dissolved in water was consumed within 2 minutes by the volunteers. Blood was taken from the volunteers at the following time points: 0: before starting the experiment; 30, 60, 90 and 120 minutes after drinking the D-glucose solution. The blood was centrifuged immediately after sampling, and blood glucose, insulin (immunoreactive insulin: IRI), liver and kidney functions, and fat related examination factors were analyzed by BML (Shibuya, Tokyo, Japan). Statistical analysis of the results was conducted by $t^2$ test, and $p<0.5$ was defined as the level of significance. Each experiment was conducted on a different day.

There was no significant difference between the different volunteers in liver and kidney function, and also not with regard to the fat related examination of serum. The effects of the supplement on blood glucose and insulin levels in these OGTT experiments are shown in FIGS. 1 and 2, respectively (IRI: immunoreactive insulin).

Figure 2:
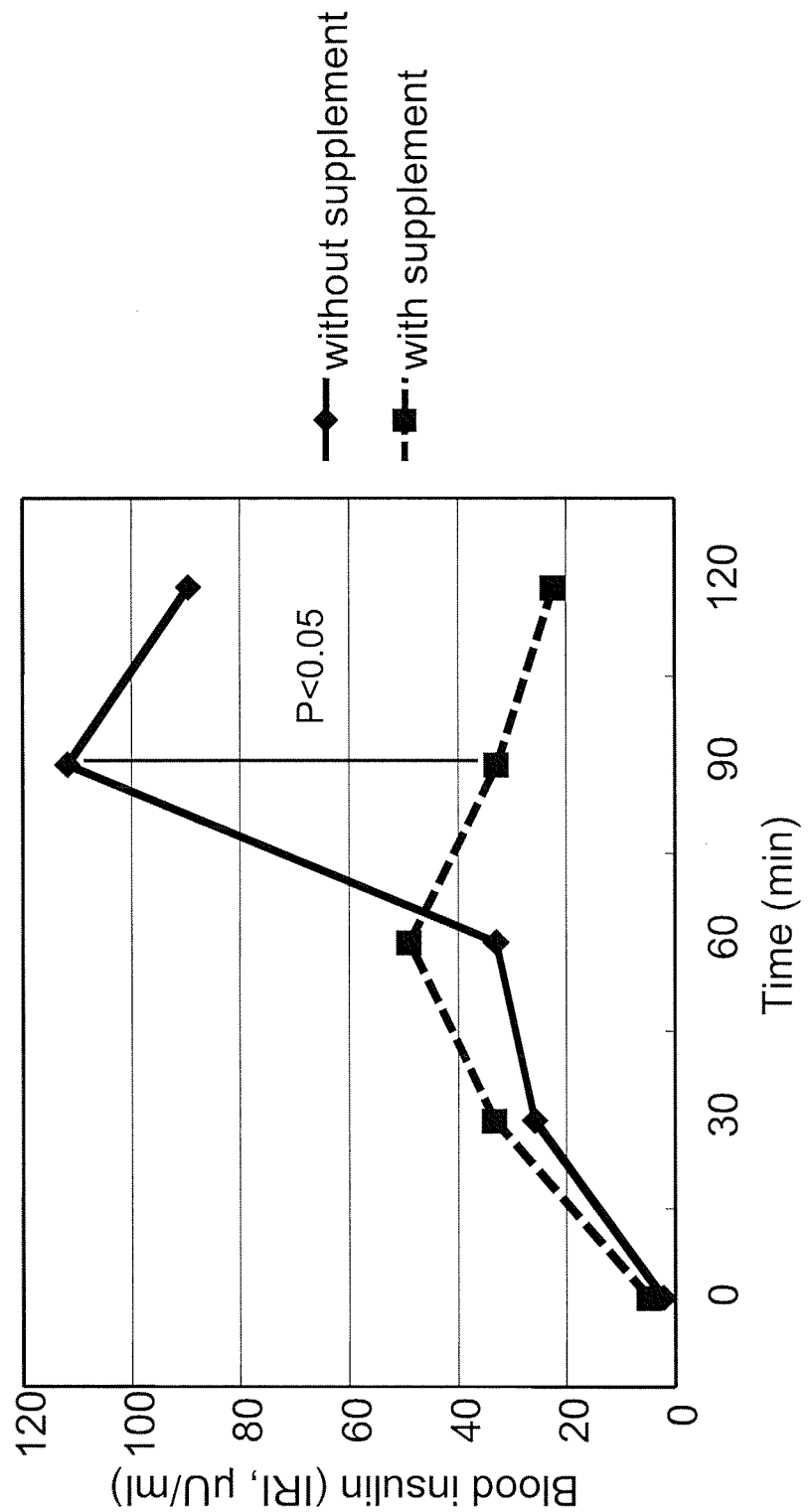
FIG. 2 is a graph of blood insulin levels during an oral glucose tolerance test (OGTT) with or without supplement.

As shown in FIG. 1, when the supplement was consumed, blood glucose levels increased only moderately after a meal and returned to normal levels earlier in comparison to control volunteers not having consumed the supplement. Thus, the supplement shields the human body from excessive blood glucose levels and reduces the retention time of glucose in the blood. In addition, these benefits were achieved with lower blood insulin level (FIG. 2), indicating that secretion of less insulin was sufficient to clear glucose from the blood after a meal. Patients with reduced pancreas function with regard to insulin production and/or secretion will thus benefit from the compositions described.

Example 2

Oral Glucose Tolerance Test (OGTT) and Snack Bread Test

Figure 3:
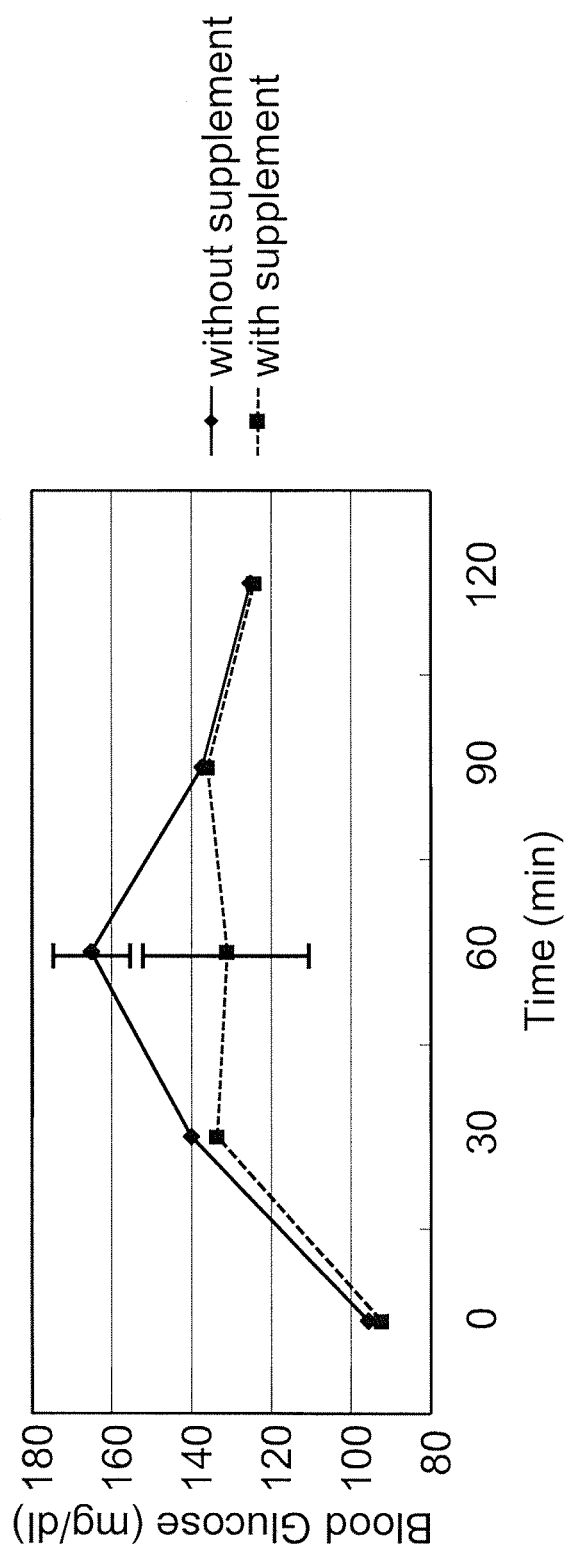
FIG. 3 is a graph of blood glucose levels following food intake with or without supplement.
Figure 4:
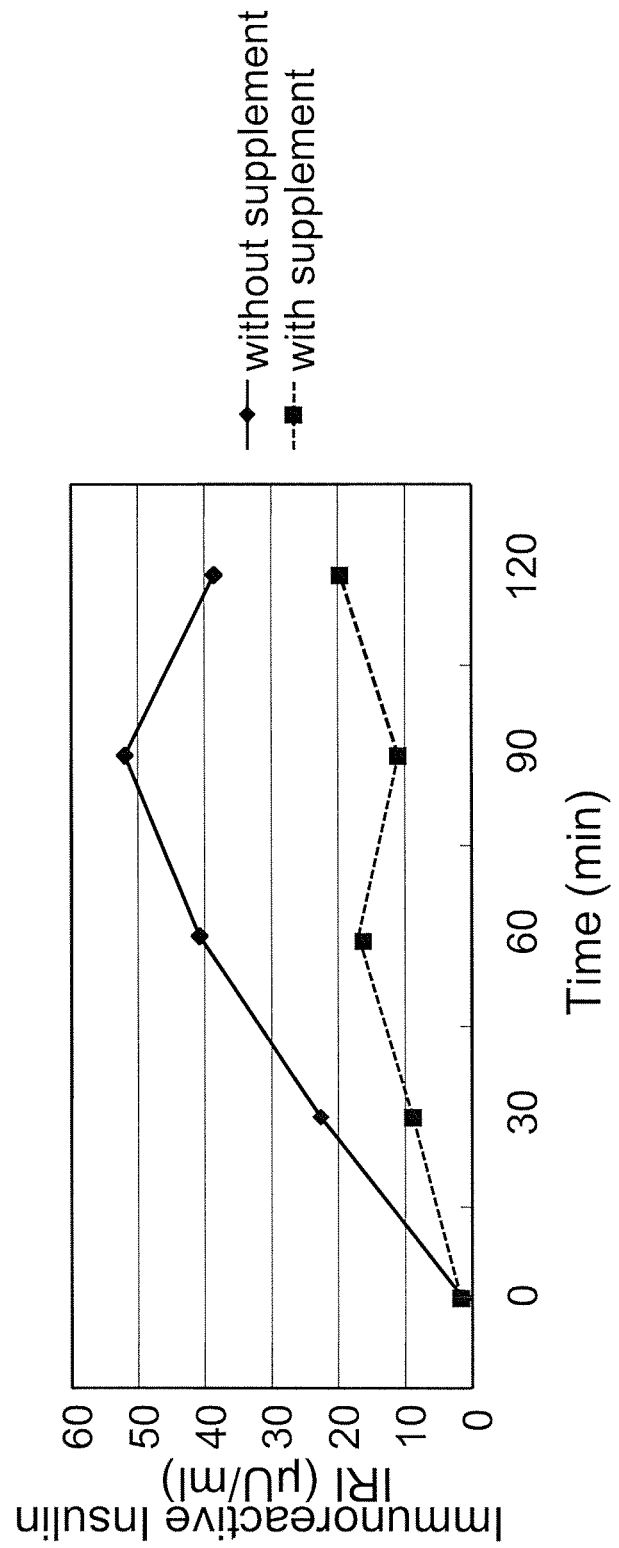
FIG. 4 is a graph of blood insulin levels following food intake with or without supplement.

For the snack bread test, one bread with adzuki paste and one with sweet cream per volunteer were used. Total nutrition facts of two breads were: calories: 780 Kcal, protein: 20 gram, fat: 18 gram, carbohydrate: 130 gram. Two snack breads were eaten by each volunteer within 10 minutes, and blood sampling was performed at the same time points as described in Example 1. Statistical analysis of the results was conducted by $t^2$ test, and $p<0.5$ was defined as the level of significance. The effects of the supplement on blood glucose and insulin levels in the snack bread experiments are shown in FIGS. 3 and 4, respectively (IRI: immunoreactive insulin). Consistent with the OGTT results in Example 1, the supplement provided the same advantageous effects to the volunteers when consuming more complex food: Blood glucose peaks were reduced, blood glucose was cleared earlier from the blood, and less insulin was needed for glucose clearance.

Based on the results of Examples 1 and 2, the fact that elevated blood glucose levels are much more rapidly cleared from the blood when using the supplement makes the compositions described herein ideal for the treatment of disease states associated with hyperglycemia.

Example 3

Comparison of Supplement Containing L-Glutamic Acid or L-Glutamine

To examine whether it makes any difference in effect on OGTT glucose degradation if L-glutamic acid or L-glutamine is used in the supplement, L-glutamine was used instead of L-glutamic acid in the supplement in some tests. Blood glucose and IRI was monitored in these glutamine mix experiments as well. Statistical analysis of the results was conducted by $t^2$ test, and $p<0.5$ was defined as the level of significance.

Figure 5:
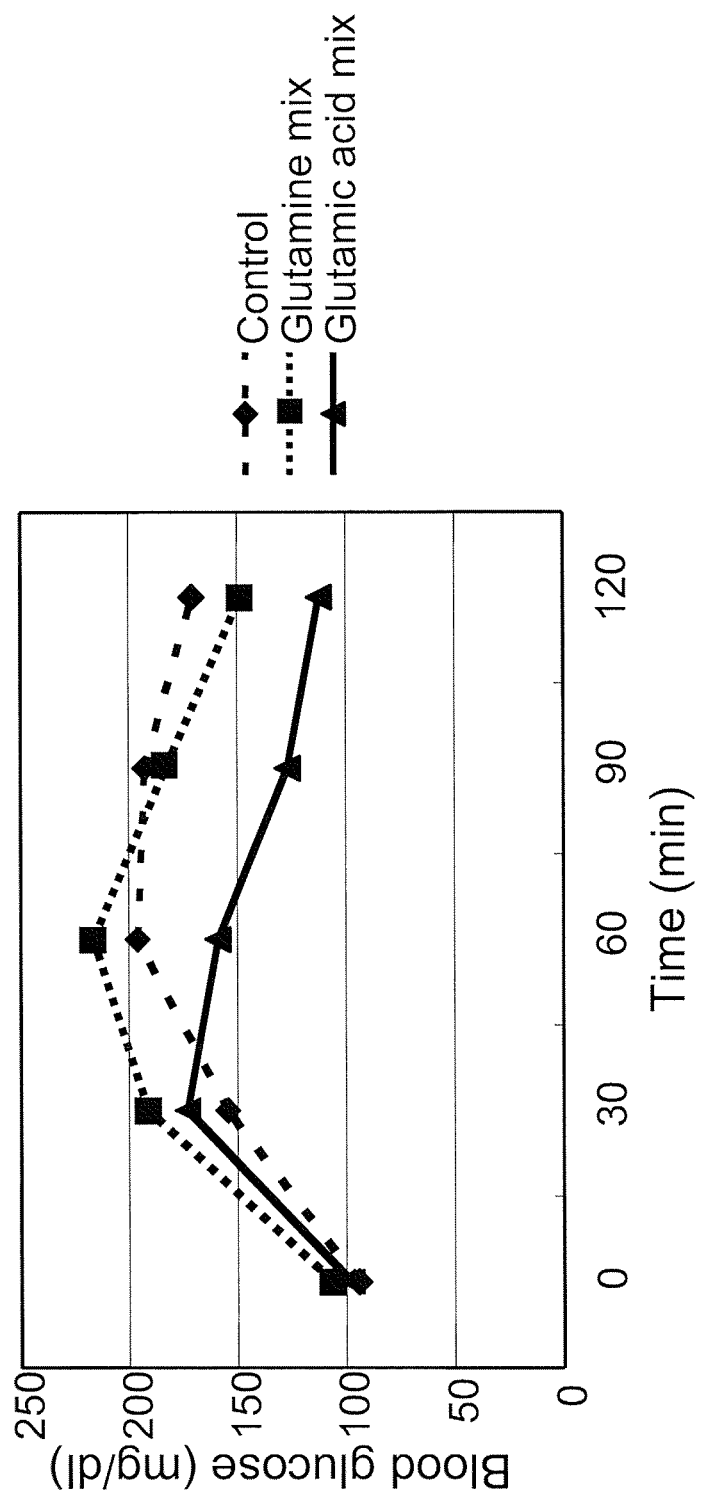
FIG. 5 is a graph of blood glucose levels during an oral glucose tolerance test (OGTT) with or without supplement containing glutamine or glutamic acid.
Figure 6:
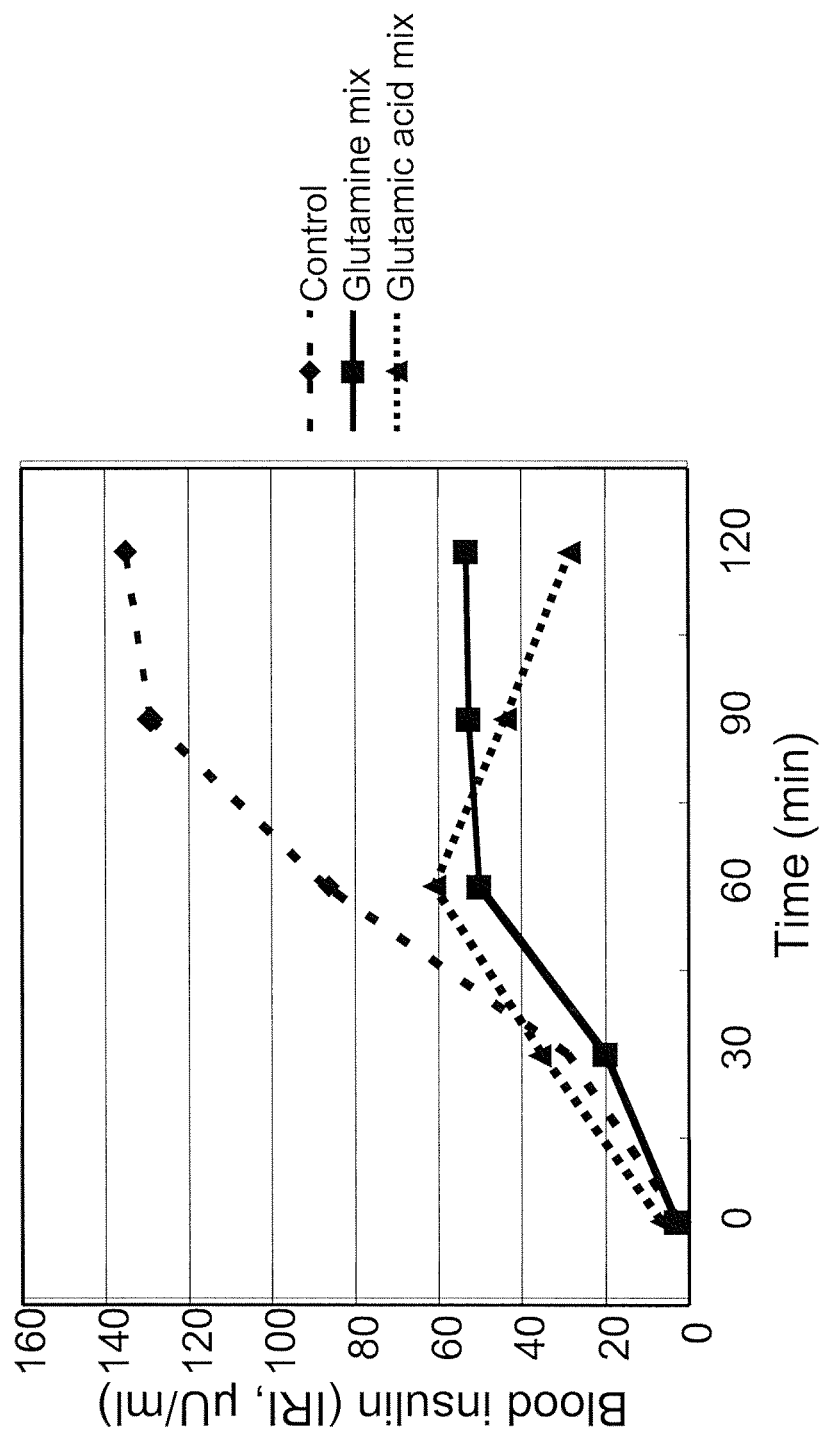
FIG. 6 is a graph of blood insulin levels during an oral glucose tolerance test (OGTT) with or without supplement containing glutamine or glutamic acid.

A comparison of the effects of supplement containing L-glutamic acid or L-glutamine mixture on blood glucose and insulin levels is shown in FIGS. 5 and 6, respectively (IRI: immunoreactive insulin; Glutamine mix: supplement with glutamine but without glutamic acid; Glutamic acid mix: supplement with glutamic acid but without glutamine; Control: OGTT without prior administration of supplement). While the supplement including glutamine instead of glutamic acid seemed not to be as effective on absolute blood glucose levels, it provided a quicker decrease in blood glucose levels with less insulin in the blood.

Example 4

Effects of Supplement on Blood Glucose in Hungry Condition

To evaluate whether or not the supplement can cause a too low blood glucose level (hypoglycemia), the supplement was taken by volunteers in hungry condition, but without anything additional to eat or drink. Blood glucose and IRI were monitored at the same time points as for the blood sampling for the OGTT.

Figure 7:
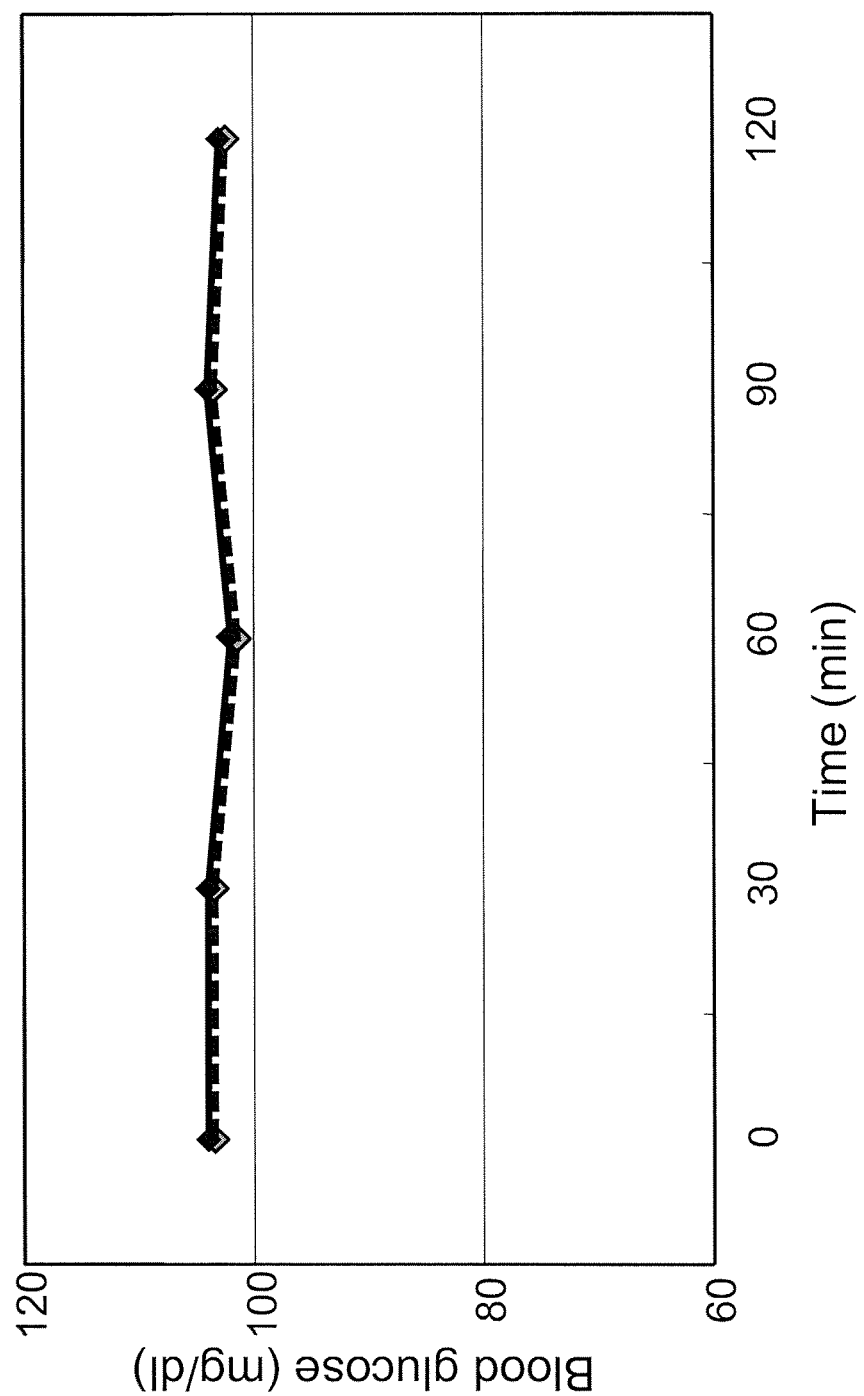
FIG. 7 is a graph of the effects of supplement on low blood glucose levels.

Blood glucose levels were stable throughout the experiments, and no side effects of too low blood glucose were detected. The blood insulin level was also low and stable (data not shown). This means that the supplement does not cause too low of a blood glucose level per se, and the blood glucose controlling effects of the supplement are limited to excess levels of blood glucose only. The effect of the supplement on blood glucose levels of volunteers in hungry condition is shown in FIG. 7. It is apparent that the blood glucose levels were not affected, and no hypoglycemia was created by the supplement when the volunteer was hungry, i.e., if blood glucose levels have returned to normal.

Example 5

Oral Glucose Tolerance Test (OGTT) with Cynomolgus Monkey

Cynomolgus monkeys underwent oral glucose tolerance test (OGTT) in two groups, either with or without administration of the supplement described in Example 1. Three animals per group were used. One hundred mg supplement/kg body weight were dissolved in 10 ml water and administered via oral-gastric intubation 10 minutes before loading glucose solution (100 mg/kg body weight) also via gastric intubation. Blood samples were collected at 0, 30, 60, 90, 120, 150, and 180 minutes after loading the glucose solution, and glucose as well as insulin levels were determined.

Figure 8:
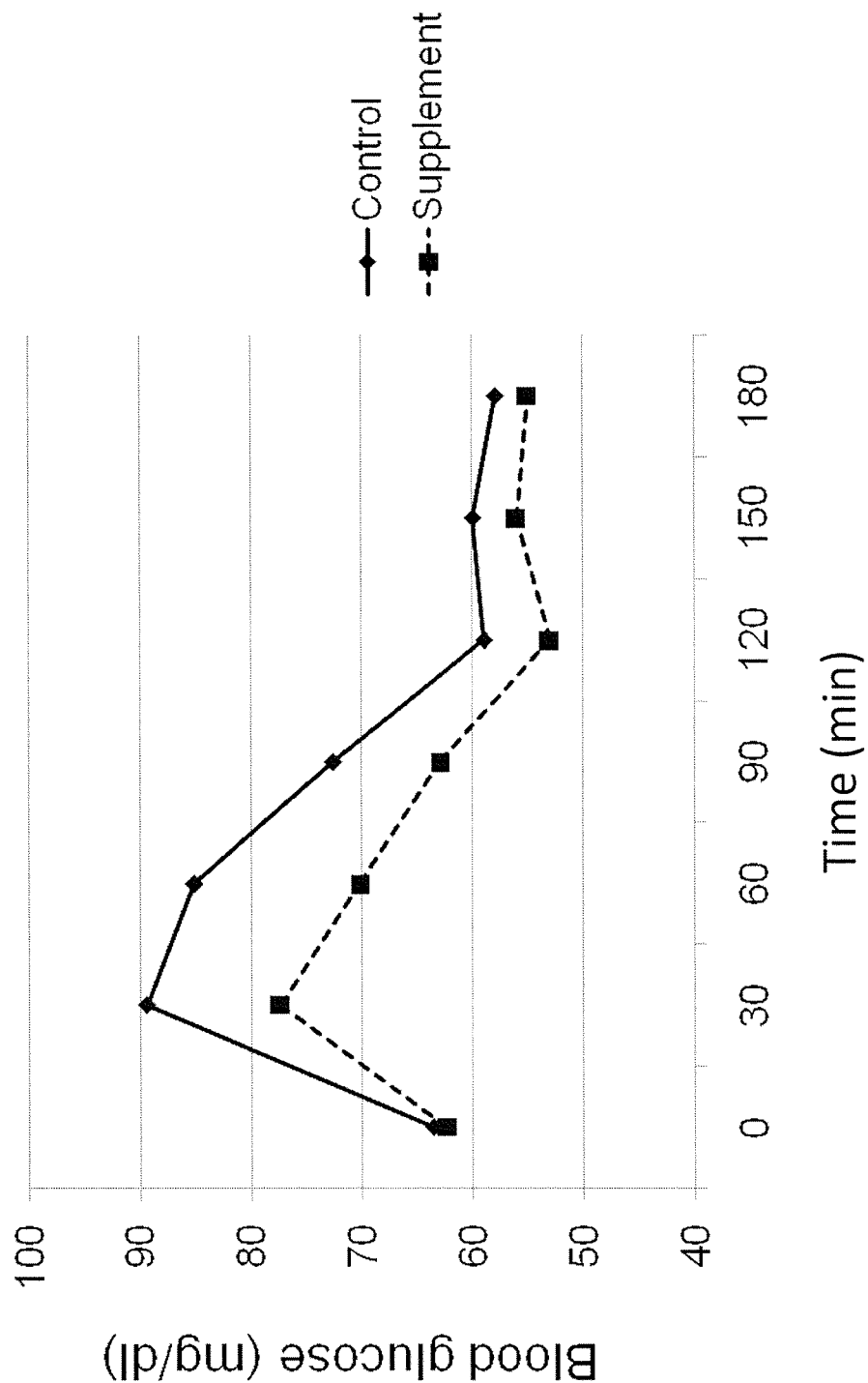
FIG. 8 is a graph of blood glucose levels during an oral glucose tolerance test (OGTT) in Cynomolgus monkeys with or without supplement.

As shown in FIG. 8, in animals having received the supplement, blood glucose levels started to decrease quickly beginning with the 30 minute time point and always maintained a lower level compared to animals that had not received the supplement ("control").

Statistical analysis of the results was conducted by $t^2$ test, and $p<0.5$ was defined as the level of significance. A statistically significant difference (t-test) was observed at the time points 30, 60, and 90 minutes after administration of the glucose solution.

Figure 9:
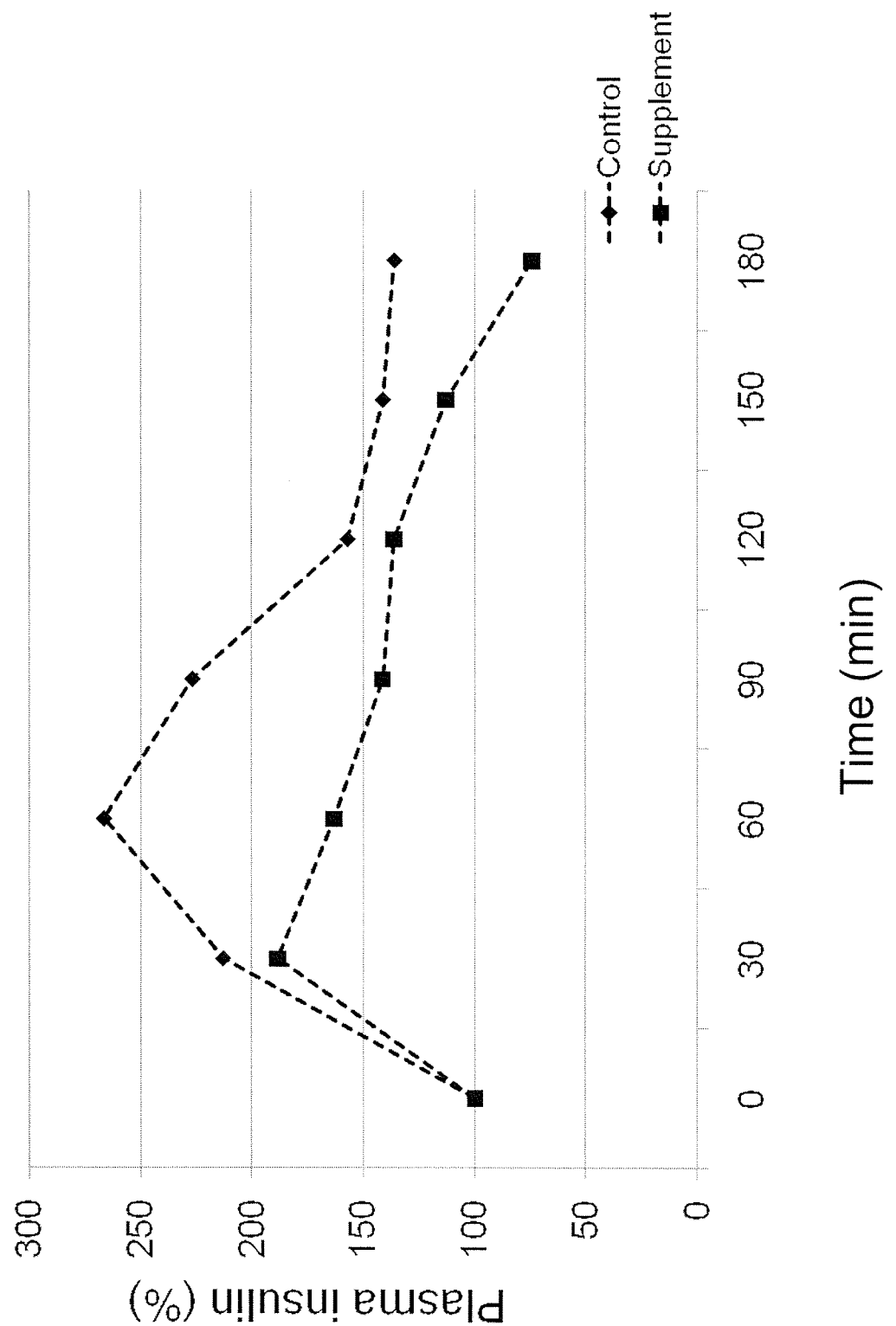
FIG. 9 is a graph of blood insulin levels during an oral glucose tolerance test (OGTT) in Cynomolgus monkeys with or without supplement.

With regard to the plasma insulin levels, as shown in FIG. 9, the group of monkeys having received the supplement showed a strong depression of blood insulin at 60 and 90 minutes after loading the glucose solution (data are plotted as relative insulin level (%)). This difference was statistically significant as determined by t-test (level of significance: $p<0.5$).

Example 6

Effects of Varying Vitamin C Concentration in the Supplement

Figure 10:
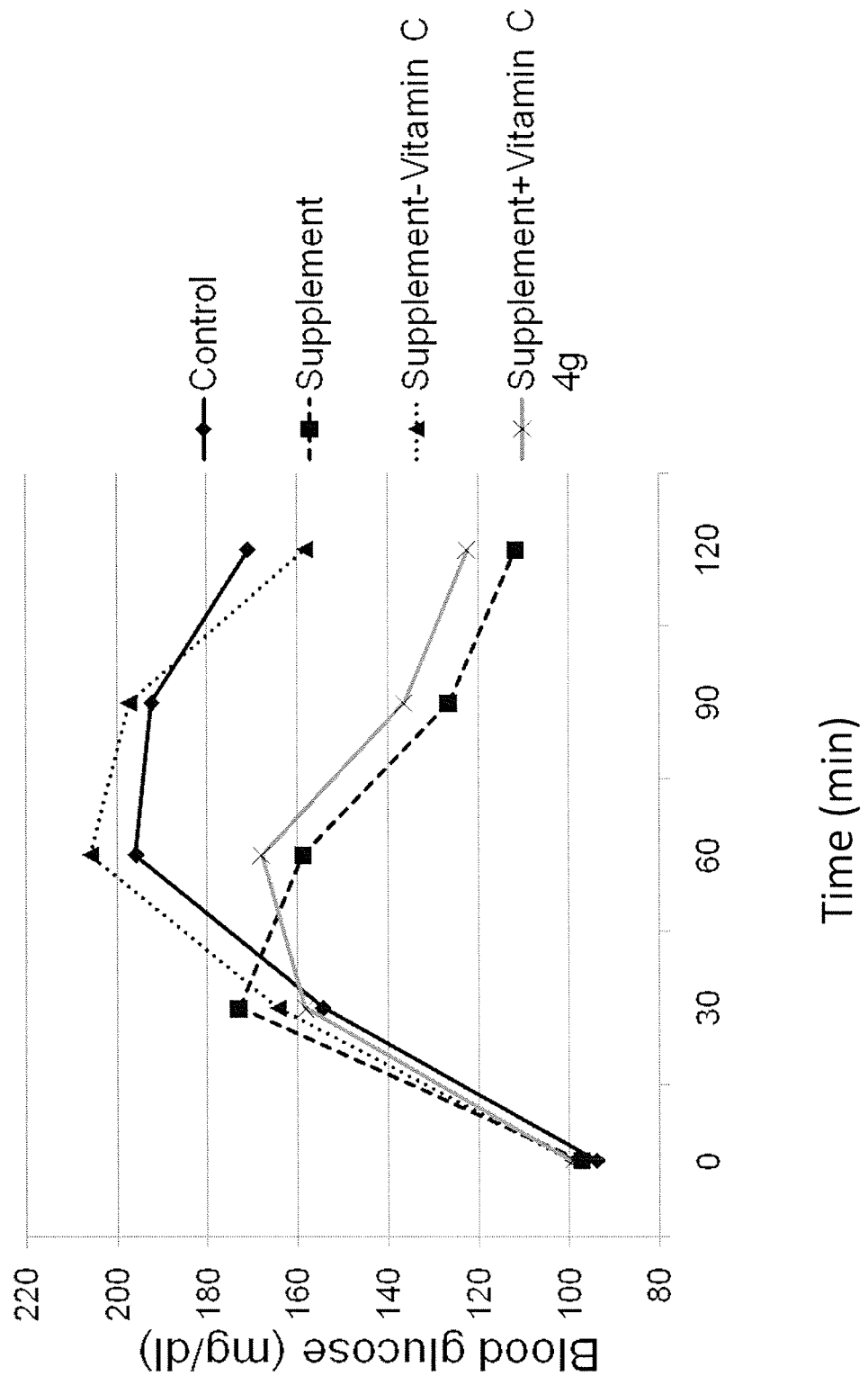
FIG. 10 is a graph of a graph of blood glucose levels during an oral glucose tolerance test (OGTT) with or without supplement either lacking vitamin C or containing different amounts of vitamin C.
Figure 11:
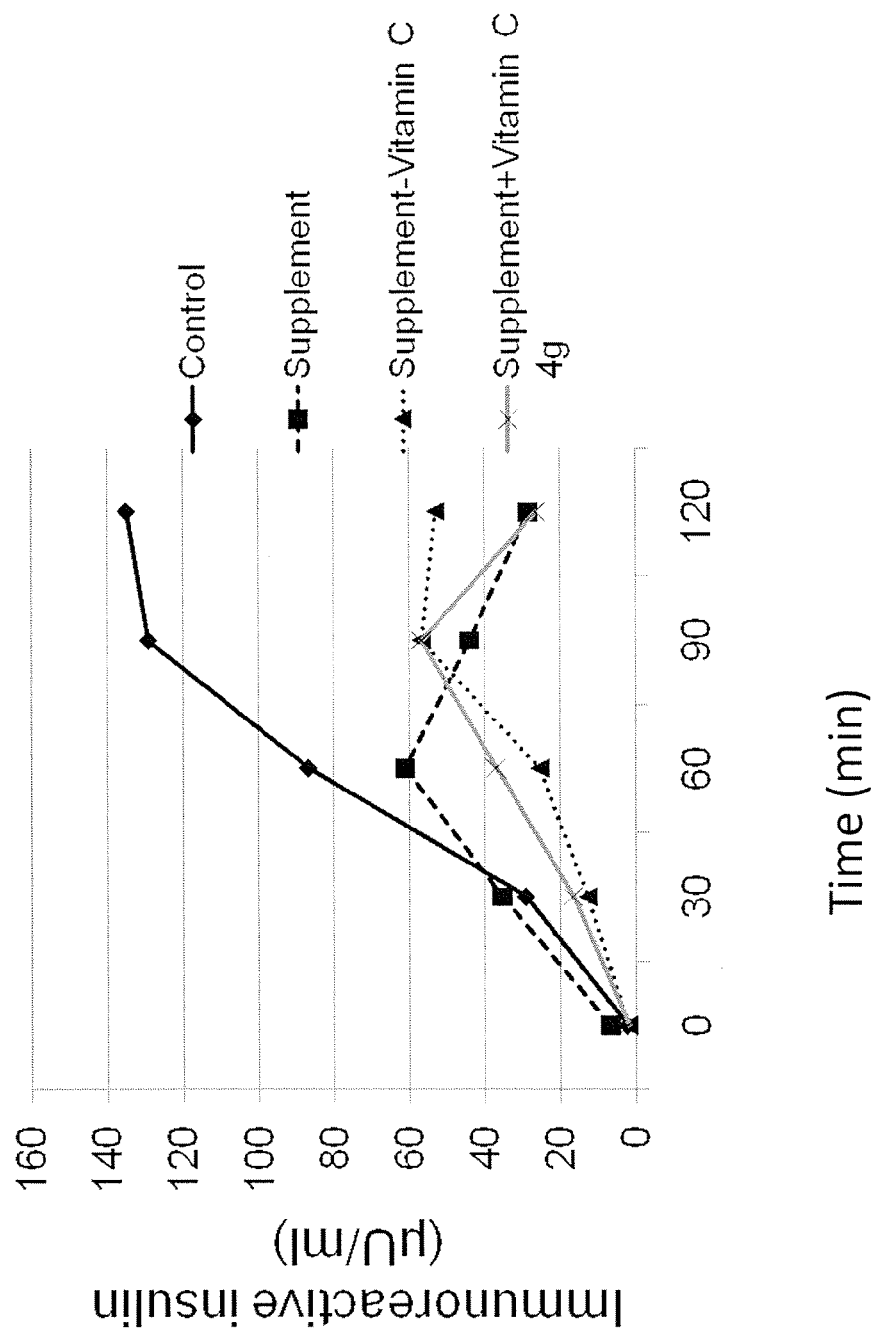
FIG. 11 is graph of a graph of blood insulin levels during an oral glucose tolerance test (OGTT) with or without supplement either lacking vitamin C or containing different amounts of vitamin C.

In order to examine the role of vitamin C in the supplement and its effects on OGTT results, experiments with three of the healthy human volunteers were conducted. The experiments were conducted as OGTT with vitamin C in the administered supplement, albeit with different amounts/concentrations. In a first round of experiments, the volunteers received the supplement described in Example 1, but supplemented with additional 4.0 g of vitamin C (total vitamin C was 5.0 g). In a later experiment, the same volunteers received the supplement described in Example 1, however without vitamin C. The supplement was taken by the volunteers 20 minutes before uptake of a D-glucose solution. Blood glucose levels and IRI levels were monitored 0, 30, 60, 90, and 120 minute after uptake of a D-glucose solution, and the results are depicted in FIGS. 10 and 11, respectively (Control: OGTT without prior administration of supplement; Supplement: OGTT with prior administration of supplement; Supplement−Vitamin C: OGTT with prior administration of vitamin C-free supplement; Supplement+Vitamin C 4 g: OGTT with prior administration of supplement with increased vitamin C content (1g+4 g=5 g)). The results were compared with data of Example 1. Statistical analysis of the results was conducted by $t^2$ test, and $p<0.5$ was defined as the level of significance.

As shown in FIGS. 10 and 11, the increase in amount of vitamin C from 1.0 g to 5.0 g in the supplement did not have any apparent impact—both supplements induced a higher blood glucose turnover rate with a reduced level of immunoreactive insulin at the same time. Furthermore, the supplement without vitamin C did not have the pronounced effect on glucose clearance from the blood as was observed for the supplement containing vitamin C. However, even without vitamin C, the supplement still reduced the demand for immunoreactive insulin in the blood in response to an increase in blood glucose, compared to the control volunteers who had not received any supplement prior to glucose challenge.

Those skilled in the art will recognize, or be able to ascertain, using no more than routine experimentation, numerous equivalents to the specific compositions and procedures described herein. Such equivalents are considered to be within the scope of this invention, and are covered by the following claims.

What is claimed is:

1. A composition for treating hyperglycemia, the composition consisting essentially of:
   (a) one or more of glutamic acid, glutamine, or a salt thereof in the total amount of 1.5 g;
   (b) one or more of cysteine or a salt thereof in the total amount of 0.5 g;
   (c) one or more of riboflavin or a salt thereof in the total amount of 0.04 g;
   (d) one or more of succinic acid or a salt thereof in the total amount of 0.1 g;
   (e) one or more of fumaric acid or a salt thereof in the total amount of 0.1 g;
   (f) one or more of niacin or salt thereof in the total amount 0.01 g;
   (g) one or more of coenzyme Q10 or a salt thereof in the total amount of 0.25 g; and
   (h) one or more of vitamin C or a salt thereof in the total amount of 1 g,
   wherein the composition treats hyperglycemia.

2. The composition of claim 1, wherein the composition is in tablet form, capsule form, powder form, or liquid form.

3. A pharmaceutical composition comprising the composition of claim 1 and a pharmaceutically acceptable carrier, excipient, or diluent.

4. A method of treating or preventing hyperglycemia in a subject in need thereof, the method comprising administering to the subject a therapeutically effective amount of the composition of claim 1, thereby treating or preventing hyperglycemia.

5. A method of treating diabetes in a subject, the method comprising administering to the subject the composition of claim 1 in combination with insulin therapy, thereby treating diabetes in the subject.

6. A method of preventing or delaying onset of symptoms of diabetes in a subject, the method comprising administering to a subject at risk of developing diabetes the composition of claim 1, thereby preventing or delaying onset of symptoms of diabetes in the subject.

7. A method of preventing or delaying onset of symptoms of diabetes in a subject, the method comprising identifying a subject at risk of developing diabetes, and administering to the subject the composition of claim 1, thereby preventing or delaying onset of symptoms of diabetes in the subject.

* * * * *

UNITED STATES PATENT AND TRADEMARK OFFICE
CERTIFICATE OF CORRECTION

PATENT NO.       : 8,633,192 B2
APPLICATION NO.  : 11/956407
DATED            : January 21, 2014
INVENTOR(S)      : Markus Matuschka-Greiffenclau et al.

It is certified that error appears in the above-identified patent and that said Letters Patent is hereby corrected as shown below:

Title Page, Assignee should read:

(73)    Assignee: TIMA Foundation, ~~Balzars~~ Balzers (LI)

Signed and Sealed this
Twenty-third Day of September, 2014

Michelle K. Lee
*Deputy Director of the United States Patent and Trademark Office*